US006379362B1

(12) United States Patent
Birk et al.

(10) Patent No.: US 6,379,362 B1
(45) Date of Patent: *Apr. 30, 2002

(54) INSULATED SKULL PINS

(75) Inventors: Janel A. Birk, Calabasas; Anne E. Hover, Plava Del Rev, both of CA (US)

(73) Assignee: DePuy AcroMed, Inc., Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/354,615

(22) Filed: Jul. 16, 1999

Related U.S. Application Data

(63) Continuation of application No. 08/988,082, filed on Dec. 10, 1997, now Pat. No. 5,961,528.

(51) Int. Cl.[7] .............................................. A61B 17/56
(52) U.S. Cl. ............................ 606/73; 606/54; 606/59; 602/37; 411/386
(58) Field of Search ........................ 602/17, 18, 32, 602/36, 37; 606/54, 56, 59, 72, 73, 104, 130; 411/386

(56) References Cited

U.S. PATENT DOCUMENTS

| | | | |
|---|---|---|---|
| 4,169,478 A | * 10/1979 | Hickman | .................... 606/151 |
| 4,397,307 A | * 8/1983 | Keller | |
| 4,444,179 A | * 4/1984 | Trippi | |
| 4,475,550 A | 10/1984 | Bremer | |
| 4,539,979 A | 9/1985 | Bremer | |
| 4,541,421 A | 9/1985 | Iversen et al. | |
| 4,612,930 A | 9/1986 | Bremer | |
| 4,838,264 A | 6/1989 | Bremer et al. | |
| 5,042,462 A | 8/1991 | Bremer | |
| 5,062,415 A | 11/1991 | Weatherby et al. | |
| 5,122,132 A | 6/1992 | Bremer | |
| 5,156,588 A | 10/1992 | Marcune et al. | |
| 5,180,361 A | 1/1993 | Moore et al. | |
| 5,197,965 A | * 3/1993 | Cherry et al. | .................. 606/54 |
| 5,254,079 A | 10/1993 | Agbodoe et al. | |
| 5,302,170 A | 4/1994 | Tweardy | |
| 5,318,509 A | 6/1994 | Agbodoe | |
| 5,347,894 A | 9/1994 | Fischer | |
| 5,437,612 A | 8/1995 | Moore et al. | |
| 5,549,620 A | 8/1996 | Bremer | |
| 5,632,722 A | 5/1997 | Tweardy et al. | |

FOREIGN PATENT DOCUMENTS

GB        2 213 066        8/1989

OTHER PUBLICATIONS

"RF Heating of Implanted Spinal Fusion Stimulator During Magnetic Resonance Imaging", IEEE Transactions on Biomedical Engineering, vol. 44, No. 5, May 1997, pp. 367–373.

"MRI Compatibility of ACE Cervicel Fixation Devices", Nancy Giezen, B.S. and Anne Hover, M.S., ACE Medical Company 1995.

(List continued on next page.)

Primary Examiner—David O. Reip
(74) Attorney, Agent, or Firm—Barnes & Thornburg

(57) ABSTRACT

A skull pin has a ceramic insulating portion between a titanium driving portion and a titanium tip portion. The driving portion of the skull pin terminates in a sleeve, and the ceramic insulator with a solid cylindrical shape is received such as with a press fit in the sleeve. The preferred ceramic material is zirconia. The tip portion has an opposing outer sleeve which receives the distal end of the ceramic insulator such as with a press fit. The ceramic insulator is believed to reduce or eliminate a burning sensation felt by patients during Magnetic Resonance Imaging (MRI), which may be caused by transmission of high (radio) frequency electrical signals through the prior art skull pins.

20 Claims, 2 Drawing Sheets

OTHER PUBLICATIONS

"MRI Compatibility of Cervical Fixation Devices", Frank G. Shellock, Ph.D., Signals, pp. 5–7, 1996.

"MR Imaging and Cervical Fixation Devices: Evaluation of Ferromagnetism, Heating, and Artifacts at 1.5 Tesla", Frank G. Shellock, Magnetic Resonance Imaging, vol. 14, No. 6, pp. 001–006, 1996.

ACE Cervical Traction, Tong Application Guide, 1993.

ACE Cervical Traction, Halo Ring Application Guide, 1993.

Mark's Standard Handbook for Mechanical Engineers, Ninth Edition (1987), pp. 6–148 and 6–149.

* cited by examiner

INSULATED SKULL PINS

This application is a continuation of application Ser. No. 08/988,082, filed Dec. 10, 1997, now U.S. Pat. No. 5,961,528.

BACKGROUND OF THE INVENTION

The present invention relates to skull pins for use in head fixation devices or cervical traction devices, and more particularly to the design of a skull pin which allows the cervical fixation/traction device to be better used in high powered, magnetic resonance imaging.

Cervical fixation and traction devices have long been used in medical treatment to hold a patient's head and neck in a particular stationary or immobile position. In particular, injuries to the cervical spine are typically treated by immobilization of the head and neck using some type of external cervical fixation device. Cervical traction devices typically involve relative immobilization of the head and neck followed by application of a traction force to the fixation device and therethrough to the head.

Two primary types of cervical fixation devices are "halos" and "tongs". Cervical halos have an ovular or ring-shaped support member which is circumferential or partially circumferential around the patient's head. Cervical tongs include two opposed arms which are placed for support on either side of the patient's head. Preferably, both the halo and tong devices allow the attending physician to maintain the patient's head and neck in a stationary position at any of a variety of orientations as selected by the attending physician. Either the halo or the tong may be supported from the patient's shoulders and chest with a vest and uprights. Traction forces may be applied to either the halo or more commonly the tong after placement on the patient. The assignee of the present invention provides such devices as ACE open backed halo rings, ACE closed backed halo rings, ACE-TRIPPI-WELLS tongs, ACE UNIVERSAL tongs, ACE standard tongs, ACE MARK III vests, ACE MARK IV vests and ACE halo vests.

The halo or tong is commonly attached to the patient's head with "skull pins". The skull pins have pointed tips which are directed toward bone of the patient's skull and thereby through a compression force hold the skull in a fixed position relative to the halo or tong. The skull pins are supported by and engaged in the halo or tong for controlled movement toward and away from the patient's head. Typically four or more skull pins are circumferentially spaced around the equator of the patient's head. If traction is applied, the skull pins commonly provide the traction force through a cantilevered bending force on the skull pins. The tips of the skull pins should be sterile when used so as to avoid the possibility of infection of the scalp or skin and underlying tissue at the skull pin contact locations.

Various medical imaging techniques with tomographic display have been used in diagnostic evaluation of the head and cervical spine. In the late 1980's, magnetic resonance imaging ("MRI") emerged as a promising new tomographical imaging modality for cervical spine images. MRI involves subjecting the viewed tissue to a static gradient magnetic field in the presence of second magnetic field which rotates and/or pulses with a characteristic frequency. Hydrogen nuclei or protons have a Larmour frequency in the radio frequency ("RF") range. When the second magnetic field rotates or pulses with an appropriate radio frequency, the hydrogen nuclei or protons at one plane of the static gradient magnetic field (i.e., one slice of the specimen) absorb and reemit electromagnetic radiation which can be sensed by the RF transmitting coil.

Various test sequences may be performed by the MRI device. Typical cervical spine pulse sequences include a sagittal T1 weighted spin echo series, a sagittal T2 weighted fast spin echo series, a sagittal gradient echo series. and an axial 3D gradient echo series. These sequence may be performed with and/or without magnetization transfer contrast ("MTC"), a pulse sequence used to achieve additional contrast in the image. Today, MRI is an essential technique of assessing various aspects of spinal injury and is valuable for monitoring the healing process.

A primary concern for any imaging system is the safety of the patient, and standards have been established for the amount of RF radiation in MRI which is considered "safe". Specific absorption rate ("SAR") is a dosimetric term that describes the mass normalized rate at which biological tissue is exposed to RF radiation. The SAR recommended by the United States Food and Drug Administration for the safe use of MRI systems is a whole body averaged SAR of 0.4 watts per kilogram or less averaged over the body, a SAR of 8.0 watts per kilogram or less spacial peak in any one gram of tissue, and a SAR of 3.2 watts per kilogram or less averaged over the head.

During MRI, the quality of the image generated is a second major concern. Any cervical device used in MRI must not distort the image quality generated by creating artifacts. The traditional material for cervical fixation device components, stainless steel, has produced artifacts during MRI procedures which are diagnostically unacceptable. Accordingly, titanium, aluminum, graphite, graphite composite or plastic have been used in cervical fixation devices in place of stainless steel to improve MRI image quality. For instance, skull pins today are typically made out of titanium. Other materials for skull pins have been proposed to reduce artifacts, such as a skull pin with proximal portion of boron or carbon fiber reinforced plastic and a distal portion of a single crystal alumina ceramic as disclosed in U.S. Pat. No. 4,612,930.

A third concern of cervical fixation device components is that the ferromagnetism of the components be quite small. That is, the components should not magnetically respond with a force of magnetic attraction or magnetic repulsion to the large magnetic fields produced in MRI systems, because such forces could cause movement of the patient's head and/or dislodgement of the cervical fixation device. Titanium, aluminum and non-ferromagnetic stainless steel all meet this requirement.

A fourth concern with regard to cervical fixation device components is associated with the peace of mind of the patient. Both the MRI procedure and the cervical fixation device are typically strange, new procedures for a patient who has recently been through a traumatic injury. As much as possible should be done to avoid instilling fear or panic in the patient during the MRI and cervical fixation procedures.

One reported way in which patient fear has escalated is associated with a "heating" sensation felt at the skull pin contact locations by some patients during some MRI procedures. There has generally been no evidence of redness or swelling of the scalp surrounding the skull pins in patients complaining of the "heating" sensation. At least one reported test indicates that the temperature increase of the skull pins during MRI is 1.5° C. or less, even with SAR's which exceed by as much as four times the recommended guidelines. This magnitude of temperature change is considered to be relatively minor from a physiological standpoint. Factors reported as effecting the amount of heating that occurs during MRI include the geometry of the object, the distance of the object from the transmitting RF coil, the amount of RF power transmitted and other aspects of the procedure.

With test results showing such a low temperature increase in the skull pins, it has been hypothesized that the "heating" sensation felt by some patients was instead vibration of the skull pins created by the MRI, particularly when MTC was used. The "heating" sensation was deemed likely to occur when the frequency or degree of vibration is at a certain level that stimulates peripheral nerve receptors located in the subcutaneous region that detects sensations of pain and temperature changes. It was recommended that MTC not be used in conjunction with cervical fixation devices. (See Shellock, "MRI compatability of Ace Cervical Fixation Devices", S.M.R.T. Newsletter 1995, pp. 4–7).

BRIEF SUMMARY OF THE INVENTION

The present invention is a skull pin for use with a cervical fixation device. The skull pin includes a metallic tip section attached to a rigid, non-metallic insulator. The tip section contacts a patient's head during use of the cervical fixation device. The insulator provides a high resistance to RF alternating electric current, decreasing current flow from the fixation device through the tip section during MRI. In one aspect, the skull pin includes a metallic driving portion attached to the insulator and separated by the insulator from contact with the tip. The driving portion attaches to the cervical fixation device for providing an inwardly directed biasing force to the insulator and the tip.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION OF THE PREFERRED EMBODIMENTS

Figure 1:
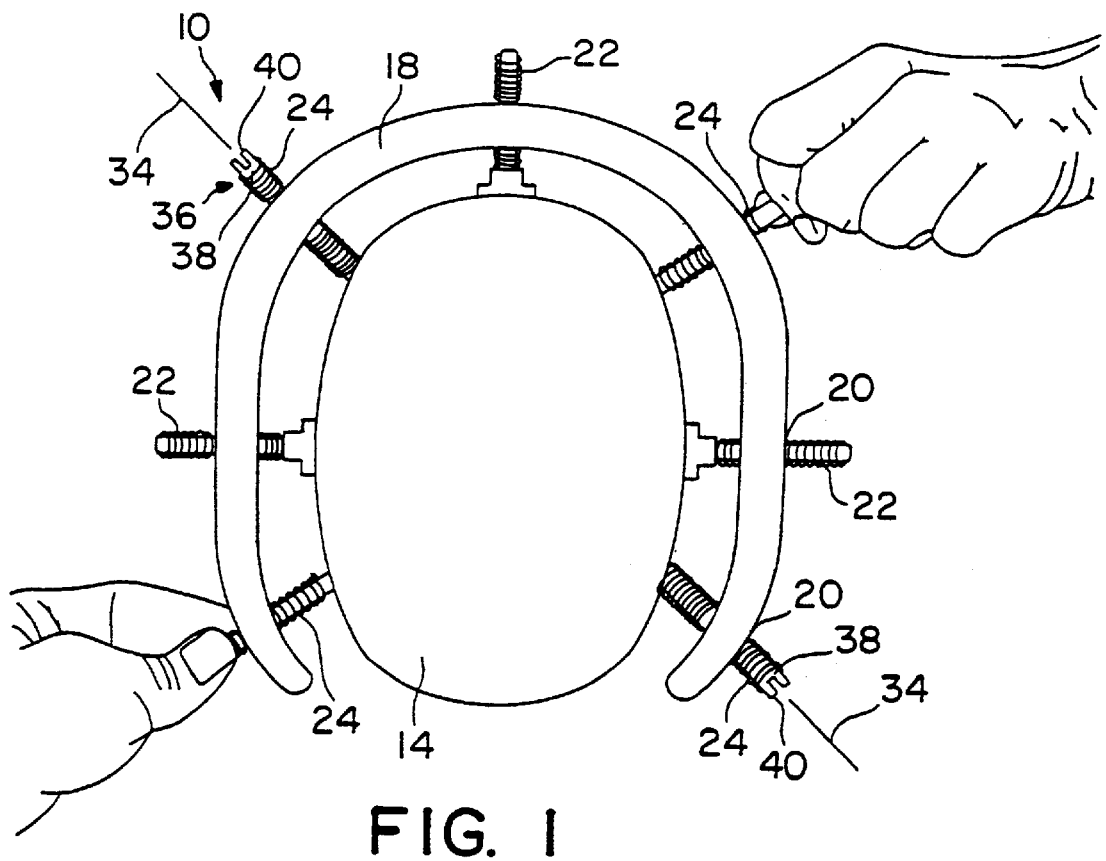
FIG. 1 shows an axial view of an ACE open back halo during tightening of the skull pins.
Figure 2:
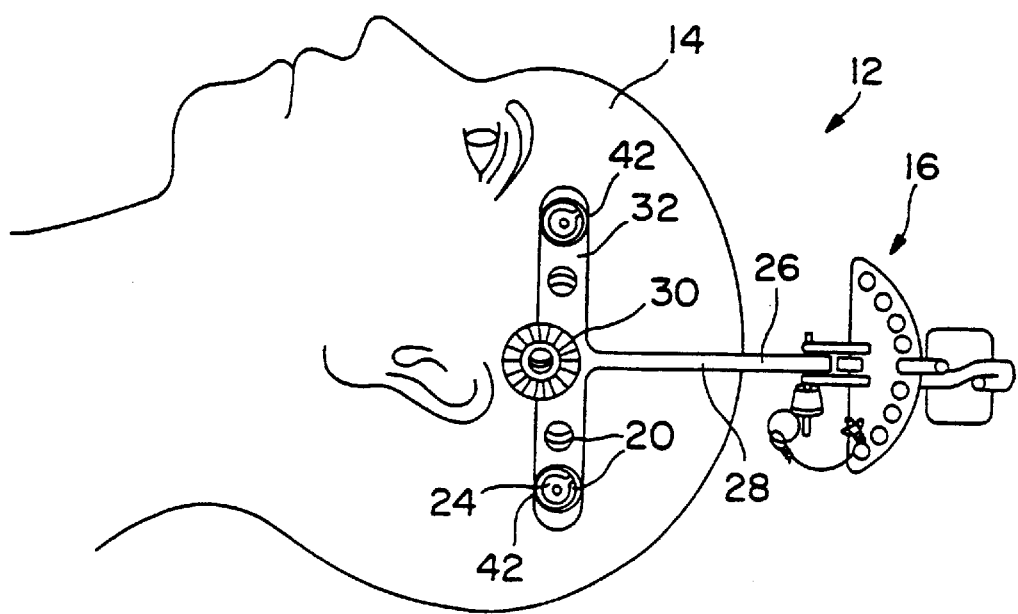
FIG. 2 is a side view of a patient's head immobilized by an ACE-TRIPPI-WELLS tong.

FIGS. 1 and 2 show typical placement of a cervical fixation device on a human head. In FIG. 1 the exemplary device is an ACE open back halo 10, while in FIG. 2 the exemplary device is an ACE TRIPPI-WELLS tong 12. Both the halo 10 and the tong 12 may be attached to a vest (not shown) with uprights (not shown), to immobilize the patient's head 14 and neck relative to his or her chest and shoulders. Preferably, both the halo 10 and tong 12 devices include adjustments 16 (shown only in FIG. 2) to allow the attending physician to maintain the patient's head 14 and neck in a stationary position at any of a variety of orientations as selected by the attending physician.

The halo 10 includes a ring 18 which may be made of a suitably strong, non-artifacting material, such as titanium, aluminum or carbon-graphite composite. The ring 18 includes a number of circumferentially spaced threaded holes 20 defined therein. Three positioning pins 22 are shown disposed at variously spaced holes 20. The positioning pins 22 are advanced in an axial direction to position the ring 18 circumferentially around the patient's head 14. The ring 18 should be positioned to provide a symmetrical fit with approximately 1 cm of clearance from the head 14. The bottom of the ring 18 should be 1 cm above the eyebrows anteriorly and parallel to the equator of the head 14. A plurality of skull pins 24 are threaded in others of the holes 20. After the skull pins 24 are tightened, the positioning pins 22 may be removed.

The tong 12 includes a center support 26 which includes two opposed arms 28 placed for support on either side of the patient's head 14. An expansion bracket 30 may be included at the ends of each arm 28. Each expansion bracket 30 may hold one or two outriggers 32, such that a plurality of threaded holes 20 are circumferentially spaced around the patient's head 14. The center support 26 should be positioned to provide a symmetrical fit with equal distance between the skull and arm 28 on both sides of the head 14, and so the holes 20 are about 1 cm above each ear and just below the equator of the head 14. Skull pins 24 may be threaded in any of the holes 20. The tong 12 may be made of a suitably strong, non-artifacting material, such as titanium, aluminum or carbon-graphite composite.

The pin contact sites should be prepared by shaving (if necessary) and anesthetization. The skull pins 24 should be sterile so as to avoid the possibility of infection of the scalp or skin and underlying tissue at the skull pin contact locations. The skull pins 24 are screwed to advance alone their axis 34. An incision may be made in the tissue at the skull pin contact location, or alternatively the skull pin 24 may pierce the tissue through its compressive force to reach the bone. In either case, the skull pins 24 are longitudinally advanced for tightening onto and into the bony skull of the patient's head 14.

Preferably the skull pins 24 include a head 36 to facilitate rotation and torqueing of the skull pins 24. For instance, the skull pins 24 may include a square head 38 for tightening with a disposable torque wrench such as to about 8 in/lb for adults. Alternatively or in conjunction with the square head 38, the head 36 of the skull pins 24 may include a slot 40 such as for receiving an ACE autoclavable torque screwdriver (not shown). Alternatively or in conjunction with the square head 38 and the slot 40, the skull pins 24 may include a knurled handle 42 (shown in FIG. 2) to facilitate finger tightening. Workers skilled in the art will recognize that many other equivalent structures exist to longitudinally advance the skull pins 24.

Figure 3:
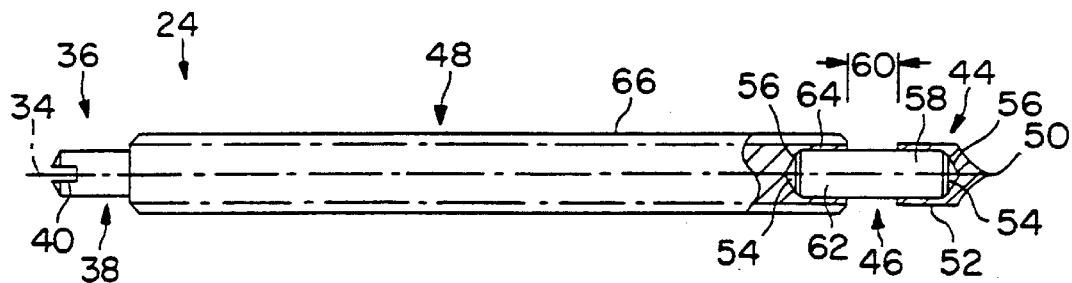
FIG. 3 is a side view in partial cross section of a first embodiment of the present invention.

A first embodiment of the skull pin 24 of the present invention is better shown in FIG. 3. While any one or more of the skull pins 24 of FIGS. 1 and 2 are according to the present invention, preferably all the skull pins 24 are in accordance with the present invention. The skull pin 24 includes a tip 44, an insulator 46 and a driving portion 48. The tip 44 includes a point 50 at its distal end for contact with the patient's head 14. The point 50 is quite sharp, for penetrating into the bony skull and perhaps also piercing tissue overlying the skull. The tip 44 is preferably circularly symmetrical about an axis 34. With circular symmetry, rotation of the skull pin 24 and the tip 44 about the axis 34 will not cause any unnecessary tissue damage and will provide for secure embedding into the skull.

At its proximal end, the tip 44 attaches to the insulator 46 such as with a hollow sleeve 52. The sleeve 52 is preferably cylindrical, such as with an inside diameter of about 0.15 inches and an outside diameter of about 0.2 inches. The opening or hole for the sleeve 52 may be formed by drilling, perhaps leaving a small drill point opening 54 at the axis 34, but a flat bearing surface 56 should be provided circumferentially around the drill point opening 54. The sleeve 52 is preferably about ⅙ of an inch long, that is, the hole in the tip 44 defining the sleeve 52 is preferably about ⅙ of an inch deep. The sleeve 52 should have a high bend strength for traction applications.

The tip 44 is preferably metallic, so it can be formed with high precision at a relatively low cost. The metallic tip 44 is durable, strong and not brittle, which is particularly important at the point 50 which contacts the bony skull and transmits significant compression forces and, for traction applications, significant cantilevered bending and/or shear forces. Forming the tip 44 of metal also allows for a sharp point 50, which reduces the amount of compression force required for tissue piercing and embedding into the bone, and also minimizes damage to the tissue and bone upon piercing and embedding. The metallic tip 44 is easily sterilized, and does not have biocompatibility problems. The metallic tip 44 should not cause artifacts in the MRI image. In the preferred embodiment, the tip 44 is formed of titanium, such as a Ti 6Al 4V/ELI in accordance with ASTM F1472 or F136 with a titanium anodize finish.

The insulator 46 includes a distal end 58 sized for mating with the sleeve 52, a central section or insulation zone 60, and a proximal end 62. The insulation zone 60 of the insulator 46 is preferably at least about ⅒th of an inch long. The preferred insulator 46 is approximately about 0.5 inch long and includes a 45° chamfer at the corners. Similar to the tip 44, the insulator 46 is preferably symmetrical about the axis 34. For instance, the insulator 46 may be a solid cylindrical shape with an outside diameter which mates with the sleeve 52 with a slight interference or press fit. Alternatively, the insulator 46 may mate within the sleeve 52 with a slight circumferential clearance, to ensure that the insulator 46 bears solidly against the bearing surface 56. However, the amount of any clearance should be minimized for best transmission of bending stresses from the insulator 46 to the tip 44 in traction applications. The insulator 46 may be further attached to the tip 44 with sealing adhesive, such as a cyano-acryllic adhesive available as LOC-TITE 4013. Alternatively, some rotational freedom of the tip 44 with respect to the insulator 46 is not detrimental to performance, but the tip 44 should not be so loose as to be able to tilt relative to the insulator 46.

The insulator 46 is made of a different material than the tip 44. In particular, the insulator 46 should be made of a material which has a relatively high electrical resistivity, and particularly a high electrical resistivity to electrical current oscillating at radio frequency. The insulator 46 must also have a high compressive strength to transmit compressive load to the tip 44 and the skull. For traction applications, the insulator 46 must also have a high bend strength. In the preferred embodiment, the bend strength of the insulator 46 matches the bend strength of the sleeves 52, 64. The preferred insulator 46 is formed of ceramic, preferably having a polycrystalline or more preferably an amorphous (i.e., non-crystalline) structure. The preferred ceramic is stabilized zirconia (yttria stabilized zirconium oxide). Zirconia has a reported conductivity $\sigma$ at 100 MHz of $5.73 \cdot 10^{-5}$/ohm·m, a reported dielectric constant at 100 MHz of 8.6, and a reported $\tan(\theta)=\sigma/2\pi f\epsilon=0.0012$, where $\theta$ is the phase angle by which output current leads voltage in degrees, f is the frequency of the input signal, and $\epsilon$ is the permittivity of the zirconia in the geometry used. The insulator 46 is cast or molded in substantially final shape, so minimal cutting, grinding or machining operations are required to complete the insulator 46.

The driving portion 48 provides the biasing force to the insulator 46 and the tip 44. At its distal end, the driving portion 48 attaches to the insulator 46 such as with a hollow sleeve 64. The inside diameter of the cylindrical sleeve 64 is sized to fit the outside diameter of the insulator 46. The sleeve 64 is preferably cylindrical, such as with an inside diameter of about 0.15 inches and an outside diameter of about 0.2 inches. The opening or hole for the sleeve 64 may be formed by drilling leaving a small drill point opening 54 at the axis 34, but a flat bearing surface 56 should be provided circumferentially around the drill point opening 54. The sleeve 64 is preferably about ¼ to ⅓ of an inch long, that is, the hole defining the sleeve 64 is preferably about ¼ to ⅓ of an inch deep. Similar to the attachment between the tip 44 and the insulator 46, the attachment between the driving portion 48 and the insulator 46 may either be with a press fit or a clearance fit, either with adhesive or not, and either allowing rotation about the axis 34 or not.

The driving portion 48 includes means for attachment with the cervical fixation device 10, 12 and for advancing the driving portion 48 along the axis 34 to provide an inwardly directed biasing force to the insulator 46 and the tip 44. Toward this end, the driving portion 48 of FIG. 3 includes screw threads 66 disposed along its outer surface. These screw threads 66 mate with correspondingly sized and pitched interior screw threads in the holes 20 of the fixation device 10, 12. The proximal end 36 of the driving portion 48 includes a square head 38 and a screwdriver slot 40, allowing alternative tools for screwing the driving portion 48 in toward the patient's head 14 during tightening, or for screwing the driving portion 48 in the opposite direction and away from the patient's head 14 during loosening.

The driving portion 48 is preferably made of a different material than the insulator 46. The driving portion 48 is preferably metallic, so it can be formed with high precision at a relatively low cost. The metallic driving portion 48 is durable and not brittle, which is particularly important at the threads 66 which transmit significant compression forces. In the preferred embodiment, the driving portion 48 is formed of titanium, such as a Ti 6Al 4V/ELI in accordance with ASTM F1472 or F136 with a titanium anodize finish.

Figure 4:
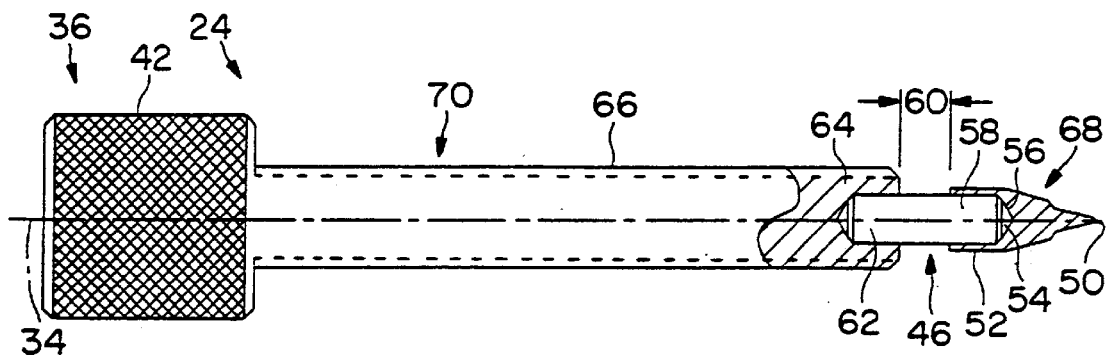
FIG. 4 is a side view in partial cross section of a second embodiment of the invention.

A second preferred embodiment of the present invention is shown in FIG. 4. The tip 68 of FIG. 4 performs the same function as the tip 44 of FIG. 3, but is shaped differently. Other than its exterior shape, the tip 68 of FIG. 4 is identical to the tip 44 of FIG. 3. The driving portion 70 of FIG. 4 has a different structure for rotation and a slightly larger outer diameter for the threads 66, but otherwise is identical to the driving portion 48 of the FIG. 3. The driving portion 70 includes a knurled cylindrical handle 42 of increased diameter, allowing the attending physician to rotate the driving portion 70 by hand without any tools.

Figure 5:
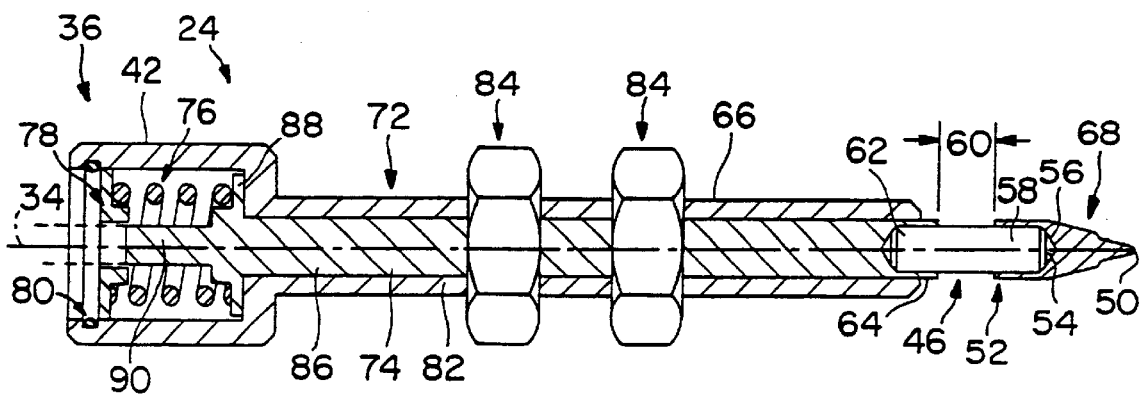
FIG. 5 is a view in partial cross section of a third embodiment of the invention.

A third preferred embodiment of the present invention is shown in FIG. 5. The driving portion 72 of FIG. 5 includes a plunger 74, a spring 76, a stop 78, a retaining clip 80, a screw sleeve 82 and two nuts 84. The distal end of the plunger 74 includes a sleeve 64 as previously described. The plunger 74 includes a smooth cylindrical shaft 86 which bears within the screw sleeve 82. The plunger 74 includes a washer 88 which extends radially outward, and the spring 76 is biased against the washer 88. A stem 90 extends axially rearward of the washer 88.

After placing the plunger 74 and the spring 76 in the screw sleeve 82 as shown, the spring 76 and plunger 74 are held in place by the stop 78 and the retaining clip 80. The stop 78 includes an axial hole slightly larger in diameter than the stem 90, allowing the stem 90 to pass therethrough upon further compression of the spring 76.

The screw sleeve 82 includes exterior threads 66 and a knurled handle 42. To tighten the skull pin 24 in place, the physician merely rotates the knurled handle 42 until the stem 90 extends an appropriate distance through the stop 78. The spring 76 ensures that an appropriate compression force is transmitted through the insulator 46 and the tip 68. The screw sleeve 82 is then retained in this axial position by tightening the nuts 84 about the fixation device 10, 12.

It should be noted in all these embodiments of FIGS. 3–5 that the outer diameter of the tip 44, 68 and the outer diameter of the insulator 46 are both smaller than the diameter of the threads 66. This allows the tip 44, 68 and the insulator 46 to be inserted into position through the hole 20 in the fixation device 10, 12, after the fixation device 10, 12 has been positioned relative to the patient's head 14.

Diagnostic evaluation of some medical conditions, such as assessing healing progress, may be performed under a controlled schedule. Other medical conditions, such as initial evaluation of injury or acute trauma, may require an immediate evaluation. Attachment of the halo 10 or tong 12 via the skull pins 24 of the present invention allows for reliable fixation of the head 14 by the attending physician with a controlled compression force and with minimal delay.

TEST EXAMPLES

Skull pins 24 of the present invention were tested on a human phantom model and compared to titanium skull pins of the prior art. All of the testing was conducted using a 1.5 tesla GE Signa 4X MRI system operating with version 5.4 software. MRI testing was performed using a quadrature body coil for the transmission of the radio frequency (RF) fields. A maximum RF heating condition was obtained by setting the following MRI parameters: fast spin-echo: plane, axial; repetition time (TR), 400 ms: echo time (TE), 13 ms: field of view (FOV), 48 cm; matrix, 512×512: number of excitations, 96; thickness, 20 mm: gap, 0 mm. The scan time was a minimum of 6 minutes. The console predicted whole-body averaged specific absorption rate (SAR) for these settings at a body weight of 150 lb was 1.002 W/kg, which is significantly higher than the SAR is for typical cervical spine imaging parameter settings.

The present invention was applied to a human phantom model which consisted of a 1.6 meter tall fiberglass shell, phantom brain, phantom muscle, phantom lungs, and phantom bone. The phantom bone was a mixture of 36% two-ton epoxy, 36% hardener (DEVCON) and 28% 2 M KCl. The dielectric constant of the bone material is 14, and its conductivity is 0.8 S/m at 100 MHz. The dielectric properties at the MRI RF frequency of 63.8 MHz were estimated to be similar to those at 100 MHz. The disks between the vertebrae were made of PVC with a dielectric constant of 2.8. To simulate brain tissue at 64 MHz, the brain was mixed with 93% $H_2O$ and 7% TX-151 (a gelling agent). The dielectric constant and conductivity of the phantom brain was 78.12 and 0.52 S/m.

A cervical fixation device was applied to the phantom body which consisted of the DEPUY ACE Medical Hybrid Halo Vest (P.N 1650) and either the extra-large ACE Open Back Halo (P/N C275), the ACE-TRIPPI-WELLS Tong (P/N 711), or the ACE UNIVERSAL Tong (P/N 820). Standard ACE titanium skull pins (P/N 1375 for halo 10, P/Ns 770 and 772 for tong 12) were used as a control. The skull pins 24 of the first embodiment (FIG. 3) were used with the open back halo 10. With the ACE-TRIPPI WELLS tong 12 and with the ACE UNIVERSAL tong 12, two skull pins 24 of the second embodiment (FIG. 4) were used on one side and two skull pins 24 of the third embodiment (FIG. 5) were used on the opposite side. Skull pins 24 with press fit and adhesively attached insulators 46 were tested separately.

Twelve Luxtron Model 3000 fiberoptic sensors were used to measure temperature at various locations. Two sensors were placed at each of the four skull pin tips 44, 68, one sensor was placed on the halo 10 or tong 12, one sensor was placed inside the head 14 of the phantom model but at least one inch away from any skull pins 24, one sensor was placed at the left rear skull pin/scalp interface, and one sensor was placed in air attached to the vest of the cervical fixation device 10, 12. Temperature measurements were taken every two seconds at all 12 sensors. The test duration included the MRI scan as well as about five minutes of base line measurements taken at the completion of test set-up but prior to commencing the MRI scan and about three to six minutes of temperature measurements taken after completion of the MRI scan.

The following table shows the results of testing for each halo 10 and tong 12 tested with standard titanium and titanium/ceramic skull pins.

| HALO OR TONG | SKULL PIN TYPE | MAX TEMP. INCREASE | LOCATION OF MAX TEMP. INCREASE |
|---|---|---|---|
| Open Back Halo | Standard Titanium | 35.5° C. | Rear Skull Pin |
| Open Back Halo | Titanium ceramic (press-fit) | 2.0° C. | Rear Skull Pin |
| Open Back Halo | Titanium ceramic (adhesive) | 2.0° C. | Front Skull Pin |
| TRIPPI-WELLS Tong | Standard Titanium | 23.5° C. | Rear Skull Pin |
| TRIPPI-WELLS Tong | Titanium ceramic (press-fit) | 0.5° C. | Air |
| TRIPPI-WELLS Tong | Titanium ceramic (adhesive) | 1.0° C. | Rear Skull Pin |
| UNIVERSAL Tong | Standard Titanium | 33.9° C. | Rear Skull Pin |
| UNIVERSAL Tong | Titanium ceramic (press-fit) | 1.0° C. | Rear Skull Pin |
| UNIVERSAL Tong | Titanium ceramic (adhesive) | 0.5° C. | Front Skull Pin |

The results of the testing show that use of cervical fixation devices in MRI can in fact cause heating associated with the titanium skull pins of the prior art when applied to the phantom body, at least during certain MRI procedures. These results are in contradiction of the reported conclusion (discussed above in the BACKGROUND section) that the heating sensation felt by some patients was merely vibration of the skull pins. A temperature change on the order of 20 to 40° C. while perhaps not high enough to cause any significant tissue damage, is certainly high enough to be felt by the patient and to create fear in the patient.

Less heating than these test results would be expected for actual patients tested under typical cervical spine imaging parameters because of two main factors: (1) the MRI parameter settings used in this testing produce significantly greater SAR values than typical settings used for imaging of the cervical spine; and (2) in actual patients, blood flow may act to dissipate heating at a higher rate seen with the human phantom model which does not simulate blood flow. However, the sensation of heating can result even though the surrounding temperatures do not change substantially, particularly at the point locations where the skull pins contact the tissue. This sensation is felt locally, where the nerves, tissue and RF energy interact.

The reason why the titanium skull pins of the prior art show heating when applied to the phantom body in the MRI is not entirely known. It is believed that the RF pulsing magnetic field of the MRI device creates an RF alternating electric current which passes through the structure of the fixation device 10, 12. Particularly when the fixation device 10, 12 is applied to the patient's head 14 at an angle to the large magnetic field gradient, it appears that an RF frequency alternating electric potential is provided along the fixation device 10, 12. The skull pins 24 provide a second electrical flow path between different locations on the fixation device 10, 12, that is, through the patient's head 14 as well as along the structure of the halo 10 or tong 12. When the electrical conductivity and/or impedance of the RF alternating electric current through these two paths are comparable, it is believed that enough current flows through the second electrical flow path (i.e., through the head tissue) at a high enough current density to heat the tissue immediately adjacent the skull pins. The amount of heating in any particular patient is a complex function of the type of MRI testing done, the power and location of the MRI RF coil relative to the patient, the quality and dimensions of the electrical connection between the skull pins and the tissue, the RF electrical resistance of the tissue, the RF electrical conductivity and capacitance of the skull pins, the material and size of the fixation device 10, 12, and the orientation of the fixation device 10, 12 relative to the large magnetic field gradient and RF coil of the MRI device.

The test results also show that the titanium/ceramic skull pins 24 of the present invention reduce the heating caused by RF energy during MRI scans. The skull pins 24 of the present invention provide both resistance and capacitance into the second electrical flow path through the patient's head. The reduced heating benefit is believed to be obtained primarily due the low dielectric constant and the low conductivity of the insulators 46 to RF alternating electric current.

Resistance measurements of the halo system to direct or low frequency current have been taken as follows:
(a) black anodized halo assembly: 20 M ohms.
(b) through patient tissue between forehead skull pins 24 against head 14 with ultrasonic lubricant at the pins: 250 k–300 k ohms.
(c) through patient tissue between back of head skull pins 24 against head 14 with ultrasonic lubricant at the pins: 500 k–600 k ohms.
(d) through patient tissue between front and back skull pins 24 against head 14 with ultrasonic lubricant at the pins: 250 k–300 k ohms. When the current is oscillated at 64 MHz, the resistance (a) of the black anodized halo assembly is reduced to about 300 ohms, while the resistances (b), (c) and (d) through patient tissue remain about the same.

The tested resistance of the zirconia insulators 46 of the present invention at 64 MHz is about 2500 Ohms, which is believed to be significant enough to effectively limit the amount of high frequency current flowing through the second path. Additionally, the dielectric constant of the insulator 46, and the geometry of the skull pin 24 including a separation of about 0.1 inches or more between the driving portion 48, 70, 72 and the tip 44, 68, is believed to provided a low enough capacitance to effective limit the amount of high frequency current flowing through the second path. It is believed that insulators made of other materials, and particularly other ceramic materials, and more particularly other polycrystalline or amorphous ceramic materials, and even more particularly other materials having a low dielectric constant and a low conductivity at 64 MHz, may similarly limit the amount of RF alternating electric current flowing through the tissue immediately adjacent the points of the skull pin tips, and produce similar beneficial reduced heating results.

Although the present invention has been described with reference to preferred embodiments, workers skilled in the art will recognize that changes maybe made in form and detail without departing from the spirit and scope of the invention. For instance, the insulator could be made longer and provide some or all of the structure of the driving portion, and/or provide some or all of the structure of the tip portion. However, the preferred insulator 46 can be manufactured at a lower cost without the need for expensive machining operations (such as threading) into the very hard material of the insulator 46.

What is claimed is:
1. A skull pin for a cervical fixation device, comprising:
   a metallic tip having a first end for contacting a patient and a second end;
   an electrically nonconductive insulator attached to the second end of the tip; and
   a driving portion having a first end, a second end and a longitudinal axis, the first end of the driving portion being attached to the insulator such that the first end of the driving portion and the second end of the tip are spaced apart along the longitudinal axis.
2. A skull pin according to claim 1, wherein the tip includes a sleeve and the insulator is located at least partially within the sleeve.
3. A skull pin according to claim 1, wherein the driving portion is titanium.
4. The skull pin according to claim 1, wherein the driving portion includes a sleeve and the insulator is located at least partially within the sleeve.
5. The skull pin according to claim 1, wherein the insulator is attached to the tip by a press fit.
6. The skull pin according to claim 1, wherein the driving portion is attached to the insulator by a press fit.
7. The skull pin according to claim 1, wherein the insulator is attached to the tip by adhesive.
8. The skull pin according to claim 1, wherein the driving portion is attached to the insulator by adhesive.
9. The skull pin according to claim 1, wherein the driving portion includes a spring plunger.
10. The skull pin according to claim 1, wherein the driving portion includes screw threads.
11. A skull pin for a cervical fixation device, comprising:
   a driving portion including a sleeve;
   a metallic tip connected to the driving portion and located entirely outside of the sleeve; and an electrically nonconductive insulator connected to the tip and the driving portion.

12. The skull pin according to claim 11, wherein the insulator is located at least partially within the sleeve.

13. The skull pin according to claim 11 wherein the tip includes a sleeve and the insulator is located at least partially within the sleeve of the tip.

14. The skull pin according to claim 11, wherein the insulator is connected to the tip by adhesive.

15. The skull pin according to claim 11, wherein the insulator is connected to the tip by a press fit.

16. The skull pin according to claim 11, wherein the insulator is connected to the sleeve by adhesive.

17. The skull pin according to claim 11, wherein the insulator is connected to the sleeve by a press fit.

18. The skull pin according to claim 11, wherein the driving portion includes a spring plunger.

19. The skull pin according to claim 11, wherein the driving portion includes screw threads.

20. A skull pin for a cervical fixation device, comprising:

a tip having a first end for contacting a patient and a second end;

an electrically nonconductive insulator attached to the second end of the tip, the insulator and the tip being constructed of different materials; and a driving portion having a first end, a second end, and a longitudinal axis, the first end of the driving portion being attached to the insulator such that the first end of the driving portion and the second end of the tip are spaced apart along the longitudinal axis.

* * * * *